United States Patent [19]

Minoz

[11] Patent Number: 6,014,578

[45] Date of Patent: Jan. 11, 2000

[54] AMBULATORY RECORDER HAVING METHOD OF CONFIGURING SIZE OF DATA SUBJECT TO LOSS IN VOLATILE MEMORY

[75] Inventor: Alain Minoz, Bromma, Sweden

[73] Assignee: Meotronic, Inc., Minneapolis, Minn.

[21] Appl. No.: 09/129,919

[22] Filed: Aug. 6, 1998

[51] Int. Cl.[7] ................................................ A61B 5/05
[52] U.S. Cl. ........................................................ 600/350
[58] Field of Search .................................. 600/300, 309, 600/343, 350, 361, 523, 561

[56] References Cited

U.S. PATENT DOCUMENTS

| | | | |
|---|---|---|---|
| D. 396,037 | 7/1998 | Cappa et al. ................. | D14/114.5 |
| 3,898,984 | 8/1975 | Mandel et al. ................. | 128/2.1 A |
| 3,941,137 | 3/1976 | Vredenbregt et al. ............ | 128/423 R |
| 4,003,379 | 1/1977 | Ellinwood, Jr. ................. | 128/260 |
| 4,082,084 | 4/1978 | Lipscher ....................... | 128/2 D |
| 4,129,125 | 12/1978 | Lester et al. .................. | 128/2.05 R |
| 4,183,354 | 1/1980 | Sibley et al. ................... | 128/711 |
| 4,198,963 | 4/1980 | Barkalow et al. ............... | 128/53 |
| 4,216,779 | 8/1980 | Squires et al. .................. | 600/523 |
| 4,333,475 | 6/1982 | Moreno et al. .................. | 128/711 |
| 4,353,375 | 10/1982 | Colburn et al. ................. | 128/782 |
| 4,365,636 | 12/1982 | Barker .......................... | 128/716 |
| 4,370,983 | 2/1983 | Lichtenstein ................... | 128/630 |
| 4,464,172 | 8/1984 | Lichtenstein ................... | 604/65 |
| 4,503,859 | 3/1985 | Petty et al. .................... | 128/635 |
| 4,529,401 | 7/1985 | Leslie et al. ................... | 604/131 |
| 4,531,527 | 7/1985 | Reinhold, Jr. et al. ........... | 128/696 |
| 4,592,018 | 5/1986 | Wiegman ........................ | 365/63 |
| 4,628,928 | 12/1986 | Lowell .......................... | 128/303 R |
| 4,632,119 | 12/1986 | Reichstein ...................... | 128/632 |
| 4,667,682 | 5/1987 | Ihlenfeld, III .................. | 128/711 |
| 4,684,367 | 8/1987 | Schaffer et al. ................. | 604/140 |
| 4,715,385 | 12/1987 | Cudahy et al. .................. | 128/710 |
| 4,748,562 | 5/1988 | Miller et al. ................... | 364/415 |
| 4,771,772 | 9/1988 | DeWitt .......................... | 128/303 R |
| 4,774,956 | 10/1988 | Kruse et al. .................... | 600/350 |
| 4,794,934 | 1/1989 | Motoyama et al. ................ | 128/734 |
| 4,895,161 | 1/1990 | Cudahy et al. .................. | 128/710 |
| 4,900,305 | 2/1990 | Smith et al. .................... | 604/65 |
| 4,917,092 | 4/1990 | Todd et al. ..................... | 128/421 |
| 4,974,599 | 12/1990 | Suzuki .......................... | 128/696 |
| 5,002,062 | 3/1991 | Suzuki .......................... | 128/696 |
| 5,007,427 | 4/1991 | Suzuki et al. ................... | 128/659 |
| 5,010,888 | 4/1991 | Jadvar et al. ................... | 128/696 |
| 5,012,411 | 4/1991 | Policastro et al. ............... | 364/413.06 |
| 5,016,636 | 5/1991 | Kulakowski ..................... | 128/644 |
| 5,042,481 | 8/1991 | Suziki et al. ................... | 128/639 |
| 5,072,458 | 12/1991 | Suzuki .......................... | 2/102 |
| 5,086,778 | 2/1992 | Mueller et al. .................. | 128/696 |
| 5,107,835 | 4/1992 | Thomas .......................... | 128/419 R |
| 5,111,396 | 5/1992 | Mills et al. .................... | 364/413.06 |
| 5,111,818 | 5/1992 | Suzuki et al. ................... | 128/644 |

(List continued on next page.)

FOREIGN PATENT DOCUMENTS 0 356 603  9/1988  Sweden ................ A61B 5/04

*Primary Examiner*—W Kamm
*Attorney, Agent, or Firm*—Thomas F. Woods; Harold Patton; Michael J. Jaro

[57] ABSTRACT

An ambulatory recorder which features a method of configuring the size of data subject to loss in volatile memory. The recorder of the present invention determines how many processor sampling cycles it will take to fill the memory buffer. As discussed above this will vary a great deal and will directly depend upon the programmed parameters, e.g. number of channels to be sampled and the various sampling frequencies. The device then determines the amount of time this number of processor sampling cycles will take. If this amount of time is greater than a pre-selected amount of time, then the number of sampling cycles is reduced to be less than the pre-selected amount of time. The recorder uses these calculations to thereby schedule the transfer of data from the volatile memory to the non volatile memory. Through such an operation the data in the memory buffer subject to loss is limited to only a pre determined amount of time, i.e. the time value of the data stored in the volatile memory is limited to a pre set value regardless of the number of channels and their frequencies from which data is recorded.

25 Claims, 6 Drawing Sheets

U.S. PATENT DOCUMENTS

| | | | |
|---|---|---|---|
| 5,113,869 | 5/1992 | Nappholz et al. | 128/696 |
| 5,117,827 | 6/1992 | Stuebe et al. | 128/635 |
| 5,131,816 | 7/1992 | Brown et al. | 417/2 |
| 5,158,083 | 10/1992 | Sacristan et al. | 128/635 |
| 5,188,104 | 2/1993 | Wernicke et al. | 128/419 R |
| 5,213,568 | 5/1993 | Lattin et al. | 604/20 |
| 5,222,503 | 6/1993 | Ives et al. | 128/731 |
| 5,224,485 | 7/1993 | Powers et al. | 128/696 |
| 5,226,431 | 7/1993 | Bible et al. | 128/904 |
| 5,228,450 | 7/1993 | Sellers | 128/711 |
| 5,238,001 | 8/1993 | Gallant et al. | 128/700 |
| 5,261,401 | 11/1993 | Baker et al. | 607/9 |
| 5,263,491 | 11/1993 | Thornton | 128/774 |
| 5,273,033 | 12/1993 | Hoffman | 607/46 |
| 5,292,344 | 3/1994 | Douglas | 607/40 |
| 5,305,202 | 4/1994 | Gallant et al. | 364/413.06 |
| 5,305,761 | 4/1994 | Byrne et al. | 128/697 |
| 5,307,263 | 4/1994 | Brown | 364/413.09 |
| 5,309,920 | 5/1994 | Gallant et al. | 128/710 |
| 5,338,157 | 8/1994 | Blomquist | 417/2 |
| 5,341,291 | 8/1994 | Roizen et al. | 364/413.02 |
| 5,343,870 | 9/1994 | Gallant et al. | 128/711 |
| 5,355,892 | 10/1994 | Saltzstein | 128/710 |
| 5,368,562 | 11/1994 | Blomquist et al. | 604/65 |
| 5,381,351 | 1/1995 | Kwong et al. | 364/571.04 |
| 5,388,587 | 2/1995 | Knutsson et al. | 128/741 |
| 5,411,022 | 5/1995 | McCue et al. | 128/632 |
| 5,429,602 | 7/1995 | Hauser | 604/65 |
| 5,431,634 | 7/1995 | Brown | 604/513 |
| 5,432,698 | 7/1995 | Fujita | 364/413.02 |
| 5,438,985 | 8/1995 | Essen-Moller | 128/633 |
| 5,479,019 | 12/1995 | Gross | 250/345 |
| 5,479,935 | 1/1996 | Essen-Moller | 128/734 |
| 5,507,904 | 4/1996 | Fisher et al. | 156/252 |
| 5,526,809 | 6/1996 | Fiddian-Green | 128/632 |
| 5,545,183 | 8/1996 | Altman | 607/5 |
| 5,607,460 | 3/1997 | Kroll | 607/30 |
| 5,645,068 | 7/1997 | Mezack et al. | 128/670 |
| 5,657,759 | 8/1997 | Essen-Moller | 128/654 |
| 5,701,894 | 12/1997 | Cherry et al. | 128/630 |
| 5,704,368 | 1/1998 | Asano et al. | 128/733 |
| 5,704,890 | 1/1998 | Bliss et al. | 600/1 |
| 5,724,025 | 3/1998 | Davori | 600/300 |
| 5,749,907 | 5/1998 | Mann | 607/27 |

AMBULATORY RECORDER HAVING METHOD OF CONFIGURING SIZE OF DATA SUBJECT TO LOSS IN VOLATILE MEMORY

FIELD OF THE INVENTION

The present invention relates to ambulatory recording, for medical and especially for diagnostic purposes, and particularly to ambulatory recorder having method of configuring size of data subject to loss in volatile memory.

BACKGROUND OF THE INVENTION

Various physiologic signals are often recorded and analyzed. These signals may included digestive pH, various digestive motility and pressure signal, EEG and EMG, to list only a few.

Typically, physicians require the concurrent recording a variety of physiologic signals. For example, gastric pH is often collected at the same time as pressure. Through the concurrent collection of various parameters the physician may better understand the patient's condition.

Ambulatory recording and recorders are widely used. Such devices include the Digitrapper Mk III™ ambulatory recorder from Synectics Medical AB, the GastroScan II™ from Medical Instruments Corporation, and the SuperLogger™ from Sandhill Scientific. These types of devices make it possible for patients to remain at home, or at the least be ambulant in a hospital setting while physiological data is recorded. Typically the devices comprise a lightweight recorder in which the desired physiological data signals are temporarily stored and later downloaded for future analysis.

Many types of physiological data may be recorded, including ECG (Electrocardiogram), EEG (Electroencephalogram) or pH and pressure (Motility) in the gastrointestinal tract. Preferably such a recorder should be able to record among a programmable number of channels at a variety of programmable frequencies.

Among the problems with current recorders, however, is that of energy usage. Such recorders, because they must be ambulatory, are battery powered.

In the particular situation of ambulatory recorders, the power consideration are further complicated by the variety of channels and frequencies from which data is desired to be sampled.

Devices which sample along a programmable number of channels and a variety of programmable frequencies along each channel present a number of difficulties. Among these difficulties lies in the management of the memory buffer such that a pre determined amount of data in the memory will be subject to possible loss. For example, if the device samples along one channel at a low frequency, the memory will take a great deal of time to be filled. Thus until this transfer takes place, the data in the memory buffer is subject to loss, for example if the device's battery fails and all power is lost.

SUMMARY OF THE INVENTION

An ambulatory recorder which features a method of configuring the size of data subject to loss in volatile memory. The recorder of the present invention determines how many processor sampling cycles it will take to fill the memory buffer. As discussed above this will vary a great deal and will directly depend upon the programmed parameters, e.g. number of channels to be sampled and the various sampling frequencies. The device then determines the amount of time this number of processor sampling cycles will take. If this amount of time is greater than a pre-selected amount of time, then the number of sampling cycles is reduced to be less than the pre-selected amount of time. The recorder uses these calculations to thereby schedule the transfer of data from the volatile memory to the non volatile memory. Through such an operation the data in the memory buffer subject to loss is limited to only a pre determined amount of time, i.e. the time value of the data stored in the volatile memory is limited to a pre set value regardless of the number of channels and their frequencies from which data is recorded.

The FIGS. are not necessarily to scale.

DETAILED DESCRIPTION OF THE DRAWINGS

Figure 1A:
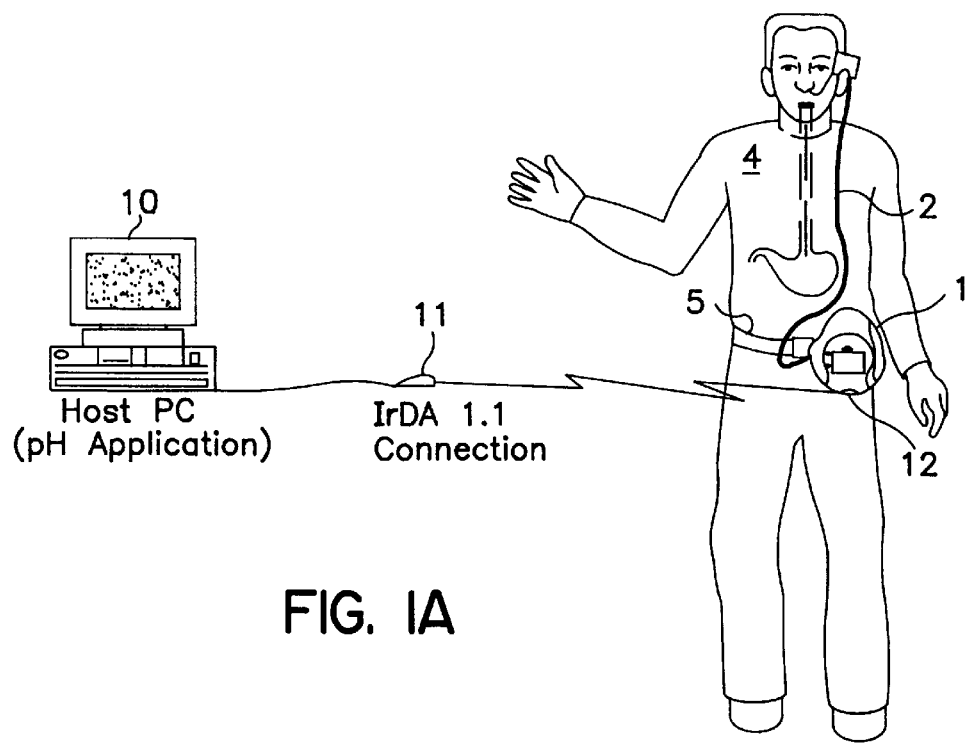
FIG. 1A depicts an ambulatory recorder of the present invention.

FIG. 1A depicts an ambulatory recorder of the present invention. As seen, ambulatory recorder 1 of the present invention may be carried by a patient. In the preferred embodiment, the recorder may be either carried through a mounting in the back of the recorder enclosure which fastens to a patient's belt 5, or the same mounting may be coupled to be carried using a shoulder harness (not shown). As seen, recorder is coupled to the patient 4 through one or more sensing catheters 2. Sensing catheters may be positioned in any area of the patient's body, from which data is to be sensed, including the esophagus, as depicted in this FIG. It should be noted, the ambulatory recorder of the present invention may be used to collect many or various types of data including gastrointestinal (including pH and pressure), neurological, as well as neuromuscular, EEG or EMG data.

Among the various sensing catheters which may be coupled to the device are manometry catheters and pH testing catheters, including the Synectics Medical AB, Stockholm, Sweden Model G 91-9 series of Multi use pH catheters; Synectics Medical AB Model G 91-2 series of Multi use pH catheters with perfusion port; or the Zinectics Inc., Salt Lake City, Utah disposable 24 pH catheter Model series G91-6 or G 91-7. While a single catheter 2 is shown depicted in this figure, recorder further permits two separate sensors to be coupled to the device, as seen in FIG. 1B.

As further seen in this figure, the recorder may also communicate with a host PC 10 via an infra red data link facility through an IrDA connection 11, for example, a JETEYE ESI-57680 available form Extended Systems, Inc., Boise, Idaho, which connects with the recorder using the infra Red Data Association 1.1 Connection Protocol. As seen, infra red data connection makes a link to infra red port 12 on recorder.

Figure 1B:
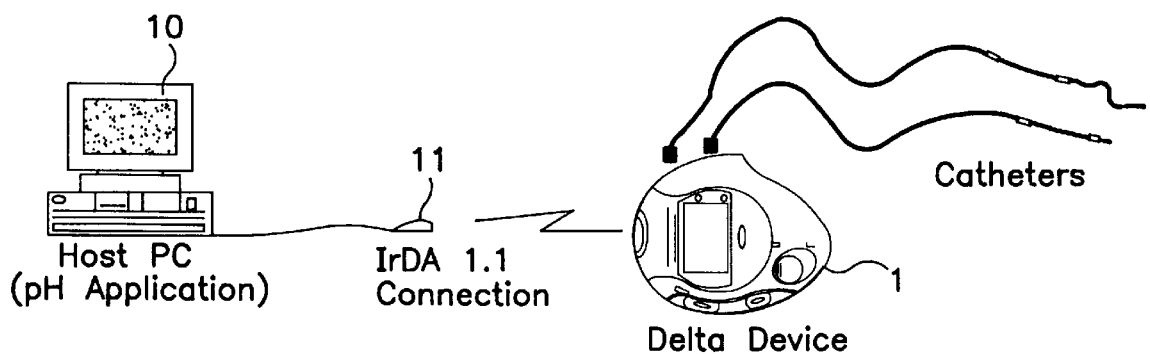
FIG. 1B illustrates a further manner in which the recorder 1 may also have an infra red data communication link made with a host PC.

FIG. 1B illustrates a further manner in which the recorder 1 may also have an infra red data communication link made with a host PC. In particular, the infra red data communication data recorder may be further made when the recorder is not worn by the patient. As discussed in more detail below, one of the advantages of the present invention is that the infra red data components and recorder case permits such a link to be made when the device is worn as shown in FIG. 1A as well as if the device is merely removed from the patient and positioned in proximity to mouse 11.

Figure 2:
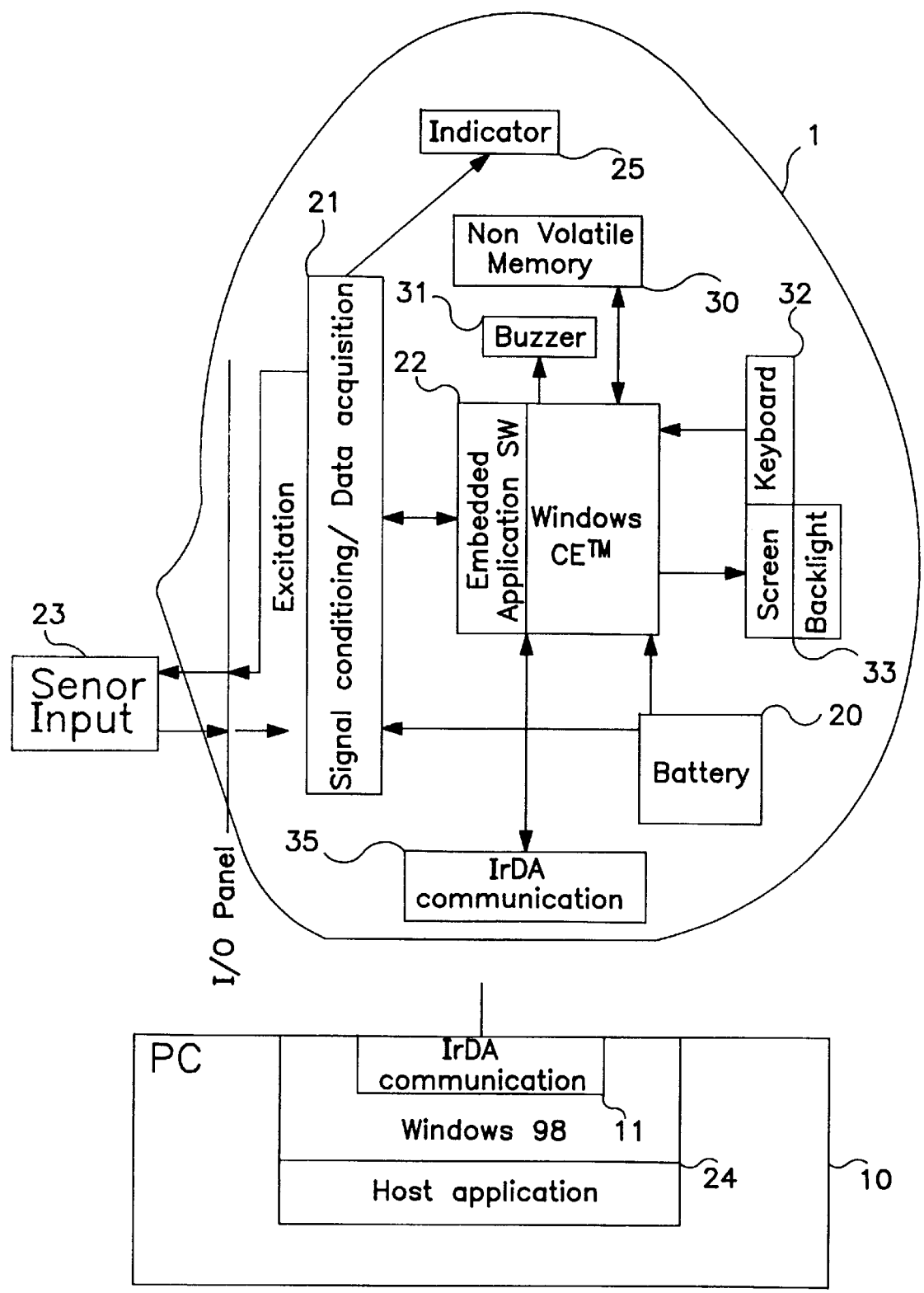
FIG. 2 is a block diagram of the data recording system shown in FIG. 1B.

FIG. 2 is a block diagram of the data recording system shown in FIG. 1B. As seen, recorder 1 features a battery 20 which is coupled to the signal conditioning/data acquisition block that is driven by a real time processor 21, the battery is coupled as well as to a non-real time processor 22 that runs the application. As disclosed in more detail below, real time processor 21 is a lower power processor which is used to sample data which is received from sensor input 23 by a sensor attached thereto (not shown in this FIG.).

Sampling is achieved through the signal conditioning providing an excitation to the sensor coupled to sensor input 23. Such excitation voltage is often used to power and, thus, permit sensing to occur in a variety of different types of sensors, including pressure sensors, as is well known in the art. The sampling and sensing controls are provided by the real time processor 21. Real time processor also drives a LED indicator 25 to show the system is running even when the screen is off.

As further seen, this processor is coupled to second non-real time processor 22. Second processor 22 is provided primarily to perform those high processing operations associated with multitasking, graphical user interface, floating point calculation, Infra Red communication and long term memory storage. In particular, second processor is primarily provided to operate a Windows CE operating system as well as one or more embedded applications, as depicted. As further seen, this processor is coupled to audible buzzer 31 as well as keyboard controls 32, a screen 33 and non-volatile memory 30. Non-volatile memory provides a long term memory for the device such that data can be recorded and preserved even if power is lost. In the preferred embodiment, keyboard controls processes a series of four push buttons, each of which provide one or more different types of system inputs, as provided by the Windows CE™ operating system, available from Microsoft Corporation, Redmond, Washington.

As further seen in this figure, recorder features an infra red port 35 to communicate with the host PC. As depicted in FIG. 1B, the infra red connection permits the recorder 1 to receive and exchange data with host PC 10. Host PC, as seen, includes both a Windows 98™ operating system available from Microsoft Corporation, Redmond, Washington, as well as one or more host applications. Host applications permit the treatment of the recorded values and help for diagnostic.

In the preferred embodiment the real time processor is the model PIC16LC67 from Microchip Technology Inc., Chandler, Ariz.; the non real time processor is the model ElanSC400 from Advanced Micro Devices, Inc. Sunnyvale, Calif.; and non-volatile memory is the model Minicard AMMCL004AWP from Advanced Micro Devices, Inc. Sunnyvale, Calif.

As discussed above, in the particular situation of ambulatory recorders, the power consideration are further complicated by the variety of channels and frequencies data is desired to be sampled from. Devices which sample along a programmable number of channels and a variety of programmable frequencies along each channel present a number of difficulties. Among these difficulties lies in the management of the memory buffer such that a pre determined amount of data in the memory will be subject to possible loss. For example, if the device samples along one channel at a low frequency, the memory will take a great deal of time to be filled. Thus until this transfer takes place, the data in the memory buffer is subject to loss, for example if the device's battery fails and all power is lost.

The recorder of the present invention determines how many processor sampling cycles it will take to fill the buffer. As discussed above this will vary a great deal and will directly depend upon the programmed parameters, e.g. number of channels to be sampled and the various sampling frequencies. The device then determines the amount of time this number of processor sampling cycles will take. If this amount of time is greater than a pre-selected amount of time, then the number of sampling cycles is reduced to be less than the pre-selected amount of time.

Figure 3:
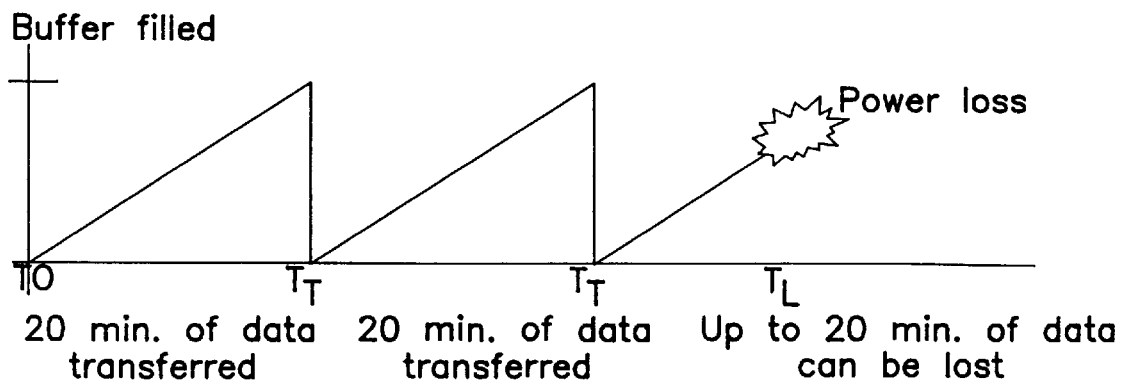
FIG. 3 illustrates the memory buffer size which increases and decreases until its contents are transferred to the non-volatile memory.

FIG. 3 illustrates the memory buffer size which increases and decreases until its contents are transferred to the non-volatile memory. As seen, starting at $T_o$, the memory buffer size increases until $T_T$ each time the contents of the buffer are transferred. This occurs again at section $T_T$. As illustrated, however, when power is lost at $T_L$ the data which had been in the volatile memory buffer is lost. In the present illustration the time between each $T_T$ is 20 minutes. Because $T_L$ occurs before the transfer of the buffer after the previous $T_T$ the amount of memory and data lost in the memory can be up to 20 minutes.

As mentioned above, the amount of actual memory buffer size is not varied, i.e. the volatile memory has a preset size. Because a variable amount of channels at variable frequencies may be sampled, the corresponding time that could be represented by the corresponding buffer in the memory would vary widely. For example, if only one channel was sampled at a very low frequency, then the buffer memory would be able to store a large time value of data. As explained above, it is important that the recorder have the ability to limit the absolute amount of time value data residing in the buffer memory so that, should power loss occur, a large amount of time value data would not be lost.

Figure 4:
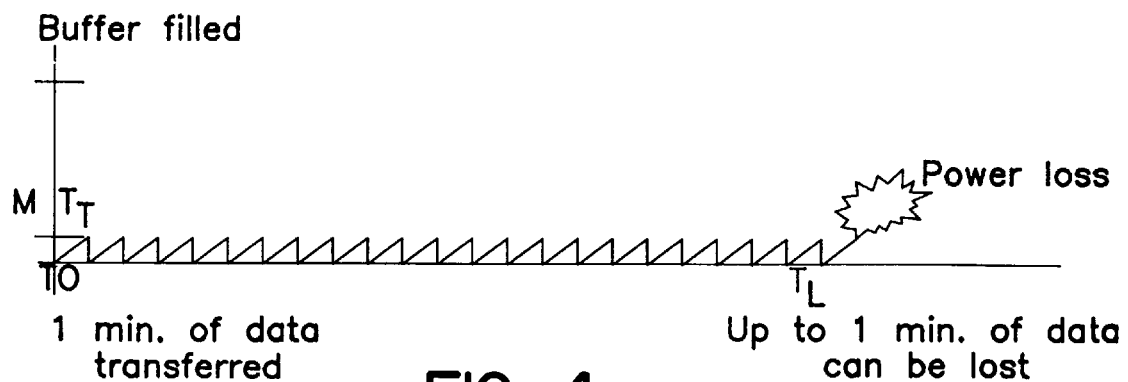
FIG. 4 illustrates the memory buffer management of the present invention.

FIG. 4 illustrates the memory buffer management of the present invention. As seen, the memory buffer is filled at a value M. Because the memory buffer is controlled such that no more than 1 minute of data is present prior to transfer, the time between transfer $T_T$ is held at 1 minutes and the buffer memory never approaches its memory buffer filled limit M. Through this control of the memory buffer no more than 1 minute of data could be lost should the volatile memory lose power.

Figure 5:
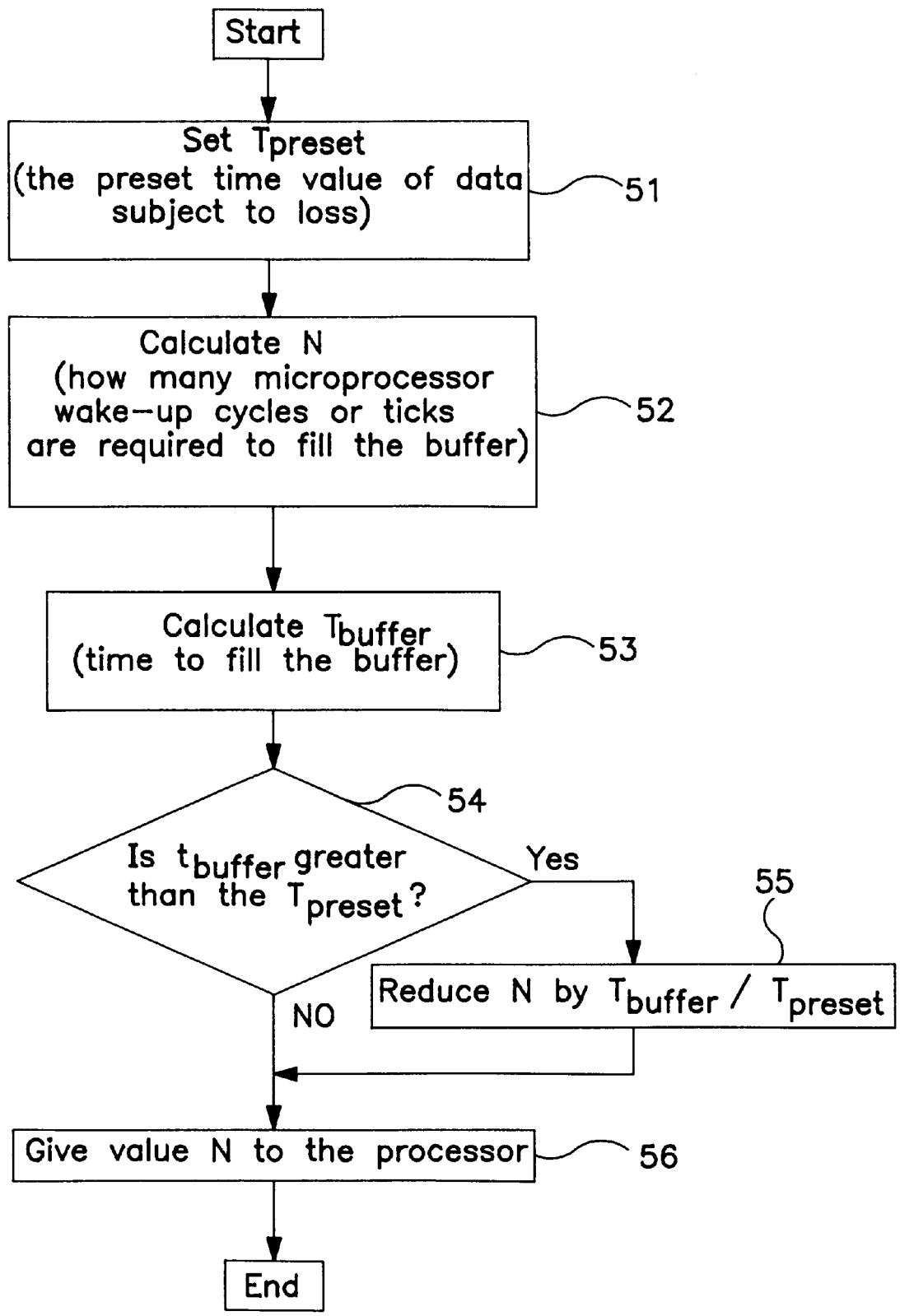
FIG. 5 is a block diagram illustrating the steps used to manage the memory buffer size such that only a preset time value of data is subject to loss.

FIG. 5 is a block diagram illustrating the steps used to manage the memory buffer size such that only a preset time value of data is subject to loss. As seen in step 51, the preset time value of data subject to loss is set as $T_{preset}$. Next, at 52 the recorder calculates how many microprocessor wake-up cycles or ticks are required to fill the buffer. This is set as N.

Next, based on N, the recorder proceeds to block 53 and determines how much time it would take to fill the buffer, designated as $T_{buffer}$. As mentioned above, because the number of channels to be sampled as well as the frequency at which the channels may be sampled can vary, the $T_{buffer}$ can vary a great deal. Next, the recorder at 54 determines if $T_{buffer}$ is greater than the $T_{preset}$. If yes, then the recorder proceeds to block 55 and reduces the number of ticks to fill the buffer by an amount corresponding to $T_{buffer}/T_{preset}$. Next, the recorder proceeds to block 56 and gives the value N to the real time processor containing the volatile memory.

Figure 6:
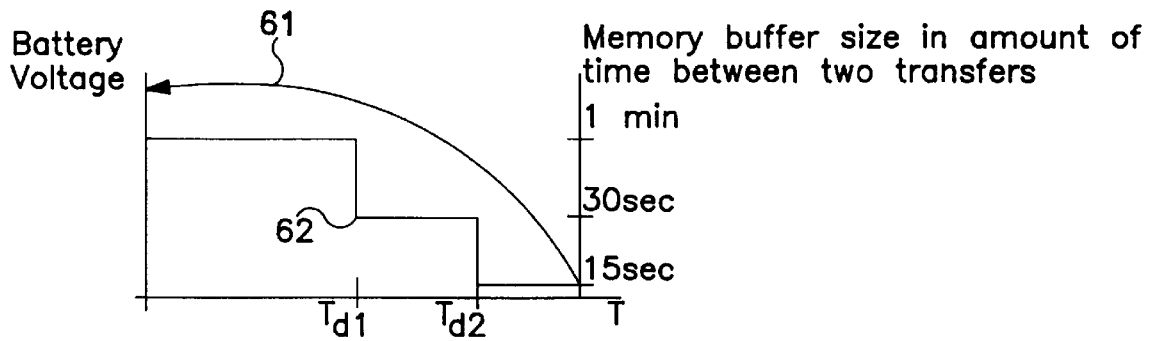
FIG. 6 illustrates an alternative method of managing the buffer memory size.

FIG. 6 illustrates an alternative method of managing the buffer memory size. In particular, in this embodiment, the memory buffer size is managed in a dynamic manner and is made larger or smaller depending upon the sensed battery voltage. Through this alternative management scheme the size of the memory buffer contents is decreased the weaker the battery becomes, such that, as the battery gets weaker, less and less time value of the data is subject to loss from the power outage. As seen in the figure, line 61 illustrates the change in battery voltage over time. Line 62 illustrates the buffer memory size available for storing sampled data. As discussed above, this initial amount of time valued data is set such that only an acceptable amount of time valued data is subject to loss, 1 minute for example. As seen at $T_{D1}$ the battery voltage has decreased and the buffer memory size is decremented such that only 30 seconds of data is stored in the buffer memory. A similar decrement in the buffer memory size is made at $T_2$ when the battery voltage again has crossed the predetermined voltage such that only 15 seconds of data is stored in the buffer memory and, thus, subject to loss upon final battery failure. Of course, the amounts of time are only used to illustrate this embodiment. other amounts and battery voltage level triggers may also be used. Battery voltage may be monitored in any acceptable fashion, such as that disclosed in U.S. Pat. No. 5,562,595 "Multiple Therapy Cardiac Assist Device Having Battery Voltage Safety Monitor" assigned to the parent of the assignee of the present invention and incorporated herein by reference.

Figure 7:
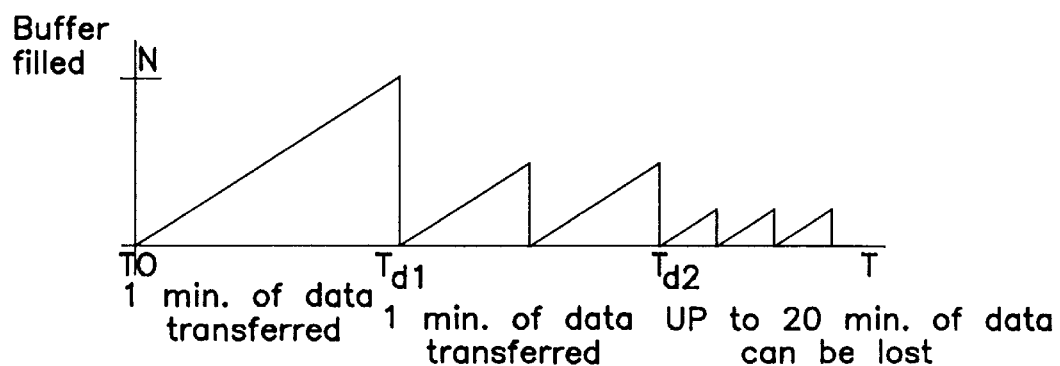
FIG. 7 illustrates the buffer memory size over time until this dynamic buffer memory management scheme is used.

FIG. 7 illustrates the buffer memory size over time as this dynamic buffer memory management scheme is used. As seen, the data sets in the buffer memory are set at $D_1$ while the battery voltage is at an acceptable level. This size buffer is maintained until time $T_{D1}$ (corresponds to FIG. 6 above), at which time the battery voltage is decreased and, thus, the amount of data permitted into the volatile memory is decreased by a predetermined amount. This action continues until time $T_{D2}$ at which time again the buffer memory size is decremented to account for the lower battery voltage such that even a similar amount of data over time is subject to loss.

Figure 8:
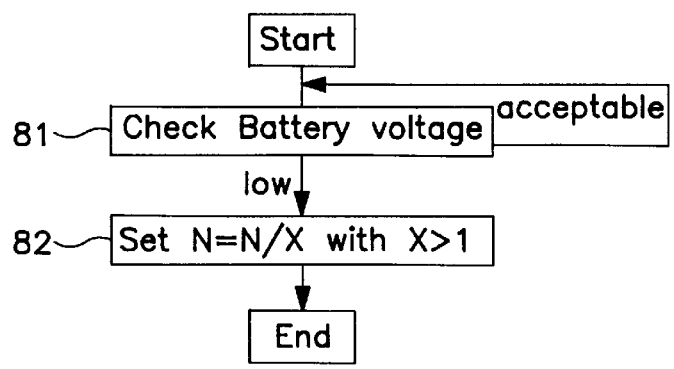
FIG. 8 depicts a flow chart through which the dynamic buffer memory management of the alternative embodiment may be practiced.

FIG. 8 depicts a flow chart through which the dynamic buffer memory management of the alternative embodiment may be practiced. As seen, at 81 the battery voltage is checked. If it is acceptable the recorder recycles itself until the next scheduled battery voltage check is performed. If the battery voltage meets the predetermined threshold, the recorder proceeds to block 82 at which N is decremented by a predetermined amount seen as N/X or X is greater than N. As will be recalled, N (as seen in FIG. 5) is set as a number of ticks to fill the buffer. This value is given to the real time processor with which the volatile buffer memory is associated so that, through this operation, the buffer memory may be made dynamically controlled by the sensed battery voltage.

Figure 9:
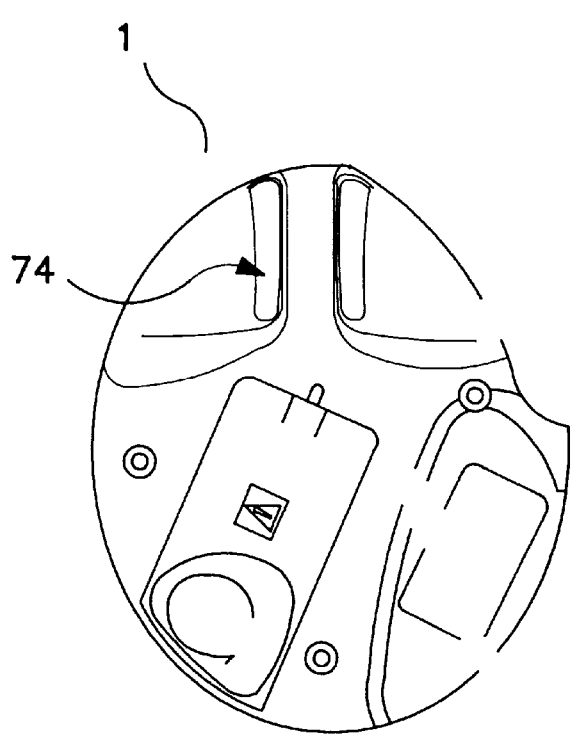
FIG. 9 is a back view of the recorder.

FIG. 9 is a back view of the recorder. As seen, recorder 1 features a belt loop 74 which may be used to mount the recorder to a patient using either the patient's belt or the shoulder strap.

Figure 10:
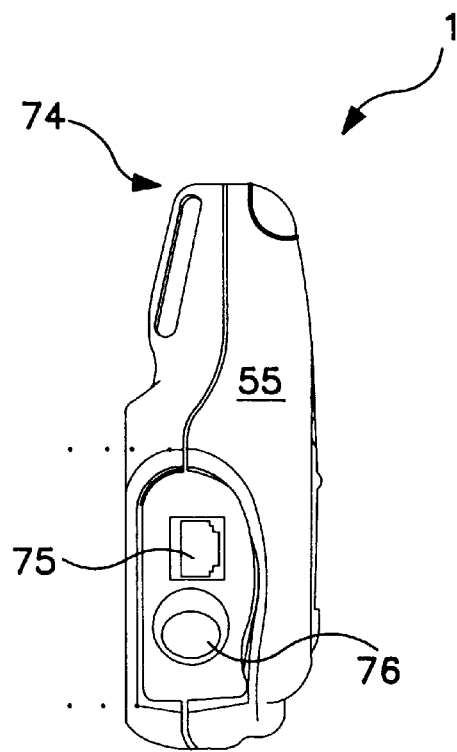
FIG. 10 is a side view of the recorder.

FIG. 10 is a side view of recorder 1. As further seen in this view, housing 55 features a pair of sensor inputs 75 and 76. In the preferred embodiment, input 75 is for a pH catheter while input 76 is for a pressure measuring catheter.

Although various embodiments of the invention have been disclosed, this is done for purposes of illustration and is not intended to be limiting with regard to the scope of the invention. It is contemplated various substitutions, alterations and/or modifications may be made to the disclosed embodiment without departing from the spirit and scope of the invention. Such modifications may include substituting elements or components which perform substantially the same function in substantially the same way to achieve substantially the same result for those described herein.

What is claimed is:

1. An ambulatory data recorder comprising:
   a sensor to sense physiologic data;
   means for sampling the sensed physiologic data;
   a volatile memory for storing the sensed physiologic data, the volatile memory having a size limit; and
   a non-volatile memory for storing the sensed data, the non-volatile memory coupled to the volatile memory so that the sensed physiologic data stored in the volatile memory is periodically transferred to the non-volatile memory.

2. The ambulatory data recorder according to claim 1 further comprising means for controlling the amount of data stored in the volatile memory such that only an amount of date collected over a pre-determined amount of time is stored in the volatile memory.

3. The ambulatory data recorder according to claim 1 wherein the means for sampling the sensed physiologic data comprises programmable means for sampling programmable number of channels of the sensed physiologic data at a programmable frequency of sampling for each of the programmed channels.

4. The ambulatory data recorder according to claim 1 wherein the means for sampling the sensed physiologic data comprises a pH sensing catheter.

5. The ambulatory data recorder according to claim 3 further comprising means for assessing the time of data which may be stored in the volatile memory before the memory is filled.

6. The ambulatory data recorder according to claim 1 further comprising means for scheduling the periodic transfer of the sensed physiologic data stored in the volatile memory to the non-volatile memory.

7. The ambulatory data recorder according to claim 6 wherein the means for scheduling comprise means for assessing the time it will take for the volatile memory size limit to be exceeded.

8. The ambulatory data recorder according to claim 1 further comprising a battery, the battery providing energy to the means for sampling the sensed physiologic data, the volatile memory, and the non-volatile memory.

9. The ambulatory data recorder according to claim 8 further comprising means for sensing the amount of energy in the battery.

10. The ambulatory data recorder according to claim 9 further comprising means for determining whether the sensed amount of energy in the battery is less than a pre determined threshold.

11. The ambulatory data recorder according to claim 10 further comprising means for decrementing the pre-determined amount of time in relation to the means for sensing the amount of energy in the battery.

12. The ambulatory data recorder according to claim 1 further comprising a mounting for mounting the ambulatory recorder to a patient.

13. The ambulatory data recorder according to claim 12 wherein the mounting comprises a loop configured for a belt or a shoulder strap to be inserted therethrough.

14. An ambulatory data recorder comprising:

a sensor to sense physiologic data;

means for sampling the sensed physiologic data;

a volatile memory for storing the sensed physiologic data, the volatile memory having a size limit; and a non-volatile memory for storing the sensed data, the non-volatile memory coupled to the volatile memory so that the sensed physiologic data stored in the volatile memory is periodically transferred to the non-volatile memory; and a processor, the processor having means for setting a time value of data which may be held in the volatile memory, the time value used by the processor to control the transfer of data from the volatile memory to the non-volatile memory.

15. The ambulatory data recorder according to claim 14 wherein the processor further comprises means for periodically turning the processor on and turning the processor off, the processor controlling the means for sampling.

16. The ambulatory data recorder according to claim 15 wherein the processor further comprises means for determining the number of data sampling operations to fill the volatile memory.

17. The ambulatory data recorder according to claim 16 further comprising means for calculating the amount of time which corresponds to the number of data sampling operations to fill the volatile memory.

18. The ambulatory data recorder according to claim 17 further comprising means for pre setting a maximum time value of data held in the volatile memory.

19. The ambulatory data recorder according to claim 18 wherein the means for comparing the pre setting a maximum time value of data held in the volatile memory with the calculated amount of time which corresponds to the number of data sampling operations to fill the volatile memory.

20. The ambulatory data recorder according to claim 14 further comprising a battery, the battery providing energy to the means for sampling the sensed physiologic data, the volatile memory, and the non-volatile memory.

21. The ambulatory data recorder according to claim 20 further comprising means for sensing the amount of energy in the battery.

22. The ambulatory data recorder according to claim 21 further comprising means for determining whether the sensed amount of energy in the battery is less than a pre determined threshold.

23. The ambulatory data recorder according to claim 22 further comprising means for decrementing the predetermined amount of time in relation to the means for sensing the amount of energy in the battery.

24. The ambulatory data recorder according to claim 14 further comprising a mounting for mounting the ambulatory recorder to a patient.

25. The ambulatory data recorder according to claim 24 wherein the mounting comprises a loop configured for a belt or a shoulder strap to be inserted therethrough.

* * * * *